United States Patent [19]

Rabenhorst et al.

[11] Patent Number: 6,133,003
[45] Date of Patent: *Oct. 17, 2000

[54] PROCESS FOR THE PREPARATION OF VANILLIN AND MICROORGANISMS SUITABLE THEREFOR

[75] Inventors: Jürgen Rabenhorst, Höxter; Rudolf Hopp, Holzminden, both of Germany

[73] Assignee: Haarmann & Reimer GmbH, Holzminden, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/702,298

[22] Filed: Aug. 23, 1996

[30] Foreign Application Priority Data

Sep. 1, 1995 [DE] Germany .............................. 195 32 317

[51] Int. Cl.⁷ .................................. C12P 7/24; C12P 7/22; C12N 1/00; C12N 1/20
[52] U.S. Cl. .......................... 435/147; 435/132; 435/170; 435/822; 435/156; 426/44
[58] Field of Search ................................... 435/147, 183, 435/132, 156, 170, 822; 426/44

[56] References Cited

U.S. PATENT DOCUMENTS 4,478,747 10/1984 Crawford et al. ......................... 435/72
5,017,388 5/1991 Rabenhorst et al. ....................... 426/44
5,128,253 7/1992 Labuda et al. ........................... 435/147
5,712,132 1/1998 Mane et al. .

FOREIGN PATENT DOCUMENTS 405197   1/1991  European Pat. Off. .
94 02 621 2/1994  WIPO .
9608576  3/1996  WIPO .

OTHER PUBLICATIONS

Sutherland et al. Can. J. Microbiol. 1983 vol. 29, pp 1253–1257.

ATCC Catalogue of Bacteria and Phages 1992 p. 25–26.

Sutherland, J.B. et al., "Metabolism of Cinnamic, P–Coumaric, and Ferulic Acids by *Streptomyces Setonii*", Canadian Journal of Microbiology, Bd. 29, Nr. 10, Jan. 1, 1983, pp. 1253–1257.

*Primary Examiner*—Leon B. Lankford, Jr.
*Assistant Examiner*—Christopher R. Tate
*Attorney, Agent, or Firm*—Joseph C. Gil; Noland J. Cheng

[57] ABSTRACT

Using newly discovered microorganisms of the family Pseudonocardiaceae, vanillin may be produced in high yields from ferulic acid. The microorganisms are two strains of Amycolatopsis.

13 Claims, No Drawings

PROCESS FOR THE PREPARATION OF VANILLIN AND MICROORGANISMS SUITABLE THEREFOR

The invention relates to a fermentative process for the preparation of vanillin from ferulic acid and to microorganisms suitable for this process.

Vanillin is an important aroma substance much used in the food and drink industry. To date it has principally been prepared from the lignin of waste sulphite liquors, occasionally also by a chemical route via oxidation of eugenol or iso-eugenol. However, the vanillin obtained in this manner has the disadvantage that it is not a natural substance within the meaning of food legislation and therefore, also, must not be labelled as a natural aroma substance.

The natural aroma substance vanillin has hitherto only been obtainable by extraction of vanilla pods; however, the natural vanillin obtained in this manner is very expensive. Natural aroma substances are chemically defined substances having aroma properties, obtained by suitable physical processes (including distillation and extraction with solvents), by enzymatic or microbiological processes from starting materials of vegetable or animal origin, which are used as such or are prepared for human consumption by conventional food processing methods (including drying, roasting, fermenting).

Various other processes for the preparation of natural vanillin using various microorganisms and enzymes have been published in the interim, but to date, because of the only very low yields or concentrations, have not resulted in any products on the market; cf. EP-A 405 197, 453 368 and 542 348, U.S. Pat. No. 5,128,253, JP-A 267 268 (Oct. 25, 1988) and 267 284 (Oct. 25, 1988).

In the scientific literature, the occurrence of vanillin in the breakdown of ferulic acid is described as an intermediate in very varied organisms, but generally no data on concentration are given; cf. S. Toms et al., "The Degradation of trans-Ferulic Acid by *Pseudomonas acidovorans*" in Biochemistry 9 (1970), 337–343; J. B. Sutherland et al., "Metabolism of Cinnamic, p-Coumaric and Ferulic Acid by *Streptomyces setonii*" in Can. J. Microbiol. 29 (1983), 1253–1257; G. Ötük, "Degradation of Ferulic Acid by *Escherichia coli*" in J. Ferment. Technol. 63 (1985), 501–506; S. Nazareth et al., "Degradation of Ferulic Acid via 4-Vinylguaiacol by *Fusarium solani* (Mart.) Sacc." in Can. J. Microbiol. 32 (1986) 494–497; M. Rahouti et al., "Metabolism of Ferulic Acid by *Paecilomyces variotii* and *Pestalotia palmarum*" in Appl. Environm. Microbiology 55 (1989), 2391–2398).

Also, some of the strains reported have not been deposited in strain collections and are therefore inaccessible for studies by other researchers.

In the search for a novel practicable preparation process for natural vanillin from readily available starting materials, it has now surprisingly been found that this is obtained economically using certain bacteria from the group of the Actinomycetes in good yields and concentrations by conversion of natural ferulic acid.

The invention therefore relates to novel species of the genus Amycolatopsis (family Pseudonocardiaceae) with the strains deposited on May 2, 1995, under the terms of the Budapest Treaty at the Deutsche Sammlung für 7 Mikroorganismen und Zellkulturen GmbH in Brunswick under the numbers DSM 9991 and DSM 9992.

On the basis of the results of the chemotaxonomic studies, both isolates were assigned to the genus Amycolatopsis (family Pseudonocardiaceae). Identification was based on the following five characteristics:

1. Diagnostic amino acid of the peptidoglycan: meso-diaminopimelic acid
2. Diagnostic sugars from whole cell hydrolysates: arabinose and galactose;
3. Mycolic acids: absent;
4. Menaquinones: MK—9 ($H_4$);
5. Fatty acid pattern: iso/anteiso-+10-methyl-branched saturated and unsaturated fatty acids plus 2-hydroxy fatty acids. This fatty acid pattern is diagnostic for representatives of the genus Amycolatopsis.

Since DSM 9991 and DSM 9992 also display the typical appearance of representatives of the genus Amycolatopsis—beige to yellow substrate mycelium and, on some media, also a fine white aerial mycelium—the assignment of DSM 9991 and DSM 9992 to the genus Amycolatopsis is additionally supported by the morphology.

Comparison of the fatty acid patterns of the two strains with the entries of the DSM fatty acid databases by principal component analysis resulted in an assignment to *Amycolatopsis mediterranei* for the two strains. However, the similarity index is too low in both cases (0.037 and 0.006) to permit definitive species assignment.

Additional analyses of the 16S rDNA and comparison of the diagnostic partial sequences with the 16S rDNA database entries of Amycolatopsis type strains supported the results of the fatty acid analyses. In the case of the 16S rDNA sequences also, high homology could not be demonstrated with the known Amycolatopsis type strains. In contrast to the fatty acid results, in which no differences were found in the patterns of the two isolates, it was possible by using the 16S rDNA sequences to differentiate DSM 9991 and DSM 9992. On the basis of the great differences in the 16S rDNA sequences (similarity 99.6%), it can be assumed that DSM 9991 and DSM 9992 are each strains of independent, previously undescribed Amycolatopsis species.

The invention further relates to a process for the preparation of vanillin from ferulic acid in the presence of novel Amycolatopsis species or their enzymes or of microorganisms having genetic material from the above Amycolatopsis species, which genetic material codes for the structural and regulatory genes for the enzymes which are active in this reaction.

The invention further relates to the use of the vanillin thus prepared for the preparation of aromas.

The natural ferulic acid preferred as starting material can be obtained, inter alia, from natural eugenol by conversion with Pseudomonas sp. DSM 7062 or DSM 7063 (DE-A 4 227 076).

The organism can be cultured in a conventional culture medium in a conventional manner for the culturing of microorganisms. The substrate can be added at the beginning of the incubation, during or after completion of growth, all at once or distributed over a relatively long period. The amount of ferulic acid is advantageously of a magnitude such that the concentration of the compound in the culture broth does not exceed 80 g/l, preferably 15 g/l. The course of the reaction can be followed by determining the starting material and the product in the culture broth by high-pressure liquid chromatography. After the optimum amount of vanillin has formed, this is isolated from the culture broth by known physical methods such as extraction, distillation or chromatography. The crude product thus obtained can be purified by further steps.

The microorganism of the invention can be cultured in synthetic, semisynthetic or complex culture media. These culture media contain carbon sources, nitrogen sources, inorganic salts and, if appropriate, trace elements and vitamins.

Carbon sources which can be used are, e.g., sugars such as glucose, sugar alcohols such as glycerol or mannitol, organic acids such as citric acid, or complex mixtures such as malt extract, yeast extract, casein or casein hydrolysate.

Examples of suitable nitrogen sources are inorganic nitrogen sources such as nitrates and ammonium salts and organic nitrogen sources such as yeast extract, soya bean meal, cotton seed meal, casein, casein hydrolysate, wheat gluten and corn steep liquor.

Inorganic salts which can be used are, for example, inter alia, sulphates, nitrates, chlorides, carbonates and phosphates of sodium, potassium, magnesium, calcium, zinc and iron.

The culture temperature is preferably in the range from 10 to 55° C., particularly preferably in the range from 35 to 45° C. The pH of the medium is preferably 3 to 9, in particular 4 to 8. The microorganisms can be cultured either in suitable shaking apparatuses or in fermenters equipped with a stirrer device. Care must be taken to ensure adequate aeration in culturing. The microorganisms can be cultured batchwise, semicontinuously or continuously. The culture time until a maximum amount of product has been achieved is between 4 and 120 hours after inoculation of the culture. To protect the microorganisms from the toxic activity of the substances used or formed, it can be advantageous to add adsorbents to the culture media, e.g. activated carbon or adsorber resins such as ®Amberlite XAD-2, ®Amberlite XAD-7, XAD-16, ®Lewatit OC 1062 or OC 1064.

The percentages in the examples below are in each case by weight.

EXAMPLES

Example 1
Preparation of the Preliminary Culture

A 500 ml conical flask with a baffle was filled with 100 ml of medium, comprising 1 g of malt extract, 0.4 g of glucose and 0.4 g of yeast extract and made up to 100 ml with water, and then sterilized for 20 minutes at 121° C. After cooling, the flask was inoculated with 200 µl of a frozen glycerol culture of Amycolatopsis sp. DSM 9991 or DSM 9992. The culture was incubated on a rotary shaking machine at 45° C. and 100 rpm. After 24 hours, this culture was used to inoculate the production medium.

Example 2
Production in the Shaking Flask

Eight 500 ml conical flasks with a side baffle were each filled with 100 ml of medium (4 g/l of glucose, 10 g/l of malt extract and 4 g/l of yeast extract) and then steam-sterilized for 20 minutes at 121° C.

After cooling, the flasks were each inoculated with 2 ml of a culture of Amycolatopsis sp. DSM 9992 from Example 1. The cultures were incubated on a rotary shaker at 37° C. and 100 rpm.

20 ml of a 3.3% strength sterile-filtered ferulic acid solution were added to each flask 16 hours after inoculation, 40 ml after 24 hours and a further 10 ml after 44 hours. After 47 hours, the flask culture broths were combined and the contents of vanillin and unreacted ferulic acid were determined.

The vanillin content in the culture broth, according to HPLC analyses, was 7317 ppm. 1526 ppm of ferulic acid were still unreacted. The final weight of the culture of the eight flasks was 1420 g. This is a conversion rate of approximately 72% of theory, based on the converted ferulic acid.

EXAMPLE 3
Production of Vanillin in the 10 l Fermenter 5 l of culture medium (4 g/l of glucose, 10 g/l of malt extract and 6 g/l of yeast extract) were sterilized in a fermenter and, after cooling, were inoculated with 100 ml of a seed culture of DSM 9992 according to Example 1.

The culture conditions were: 37° C., 500 rpm, 5 l of air/min. 12.5 hours after inoculation, 1.634 kg of an approximately 3.7% strength ferulic acid solution (60.2 g of ferulic acid) were added. After 17.5 hours, a further 4.397 kg of an approximately 3.7% strength ferulic acid solution (164.72 g of ferulic acid) were pumped in over a period of 10 hours.

After 32 hours, the fermentation was terminated. The vanillin concentration was 11.5 g/l and 1 g/l of unreacted ferulic acid was still present. The final volume was 11.29 l. This is a conversion rate of 77.8% of theory, based on converted ferulic acid.

We claim:

1. A biologically pure culture of Amycolatopsis sp. DSM 9992, or a mutant thereof which converts ferulic acid to vanillin.

2. A process for preparing vanillin comprising subjecting ferulic acid to Amycolatopsis sp. DSM 9992, or mutant thereof or an isolated enzyme thereof which converts ferulic acid to vanillin, for a period of time sufficient to convert said ferulic acid to vanillin, and recovering the vanillin thus formed.

3. The process according to claim 2, wherein said ferulic acid is natural ferulic acid.

4. A process comprising using vanillin as a flavoring, wherein the improvement comprises using as said vanillin the vanillin produced by a process according to claim 2.

5. The process according to claim 4, wherein the vanillin is produced from natural ferulic acid.

6. The process according to claim 2, wherein said microorganism is used to convert ferulic acid to vanillin, and the microorganism is contained in a medium which comprises a carbon source.

7. The process according to claim 6, wherein the carbon source is selected from the group consisting of sugars, sugar alcohols, organic acids and complex mixtures.

8. The process according to claim 6, wherein said medium further comprises a nitrogen source.

9. A process for preparing vanillin comprising subjecting ferulic acid to Amycolatopsis sp. DSM 9991, or mutant thereof or isolated enzyme thereof which converts ferulic acid to vanillin, for a period of time sufficient to convert said ferulic acid to vanillin, and recovering the vanillin thus formed, wherein if Amycolatopsis sp. DSM 9991 or mutant thereof is used to convert ferulic acid to vanillin, then the Amycolatopsis sp. DSM 9991 or mutant thereof is contained in a medium which comprises a carbon source.

10. The process according to claim 9, wherein the carbon source is selected from the group consisting of sugars, sugar alcohols, organic acids and complex mixtures.

11. The process according to claim 9, wherein said medium further comprises a nitrogen source.

12. A process comprising using vanillin as a flavoring, wherein the improvement comprises using as said vanillin the vanillin produced by a process according to claim 9.

13. A process for preparing vanillin comprising subjecting ferulic acid to a microorganism selected from the group consisting of Amycolatopsis sp. DSM 9991 or DSM 9992, or a mutant thereof or an isolated enzyme thereof which converts ferulic acid to vanillin, to convert said ferulic acid to said vanillin in a concentration of said vanillin of at least 7.317 g/l within a period of time of from 4 to 120 hours, and recovering the vanillin thus formed.

* * * * *